United States Patent [19]

Morgan

[11] Patent Number: 5,070,738
[45] Date of Patent: Dec. 10, 1991

[54] DEVICE AND METHOD FOR RECIRCULATING A STREAM OF FLUID FROM A VESSEL

[75] Inventor: James E. Morgan, Nuns' Island, Canada

[73] Assignee: Morgan Schaffer Systems Incorporated, Montreal, Canada

[21] Appl. No.: 538,222

[22] Filed: Jun. 14, 1990

[51] Int. Cl.⁵ .............................................. G01N 1/14
[52] U.S. Cl. ................................ 73/863.83; 73/863.84
[58] Field of Search ......................... 73/863.81–863.11, 73/863.71, 863.72, 864.34; 137/563

[56] References Cited

U.S. PATENT DOCUMENTS

| | | | |
|---|---|---|---|
| 2,836,068 | 5/1958 | Clift | 73/863.86 |
| 3,960,500 | 6/1976 | Ross et al. | 73/863.11 |
| 3,969,608 | 7/1976 | Day | 137/563 |
| 4,037,475 | 7/1977 | Tophan | 73/863.83 |
| 4,115,229 | 9/1978 | Capone | 73/863.11 |
| 4,669,321 | 6/1987 | Meyer | 73/863.85 |
| 4,715,236 | 12/1987 | Willert | 73/863.86 |
| 4,790,291 | 12/1988 | Barrett | 137/563 |
| 4,917,142 | 4/1990 | Laing et al. | 137/563 |
| 4,928,536 | 5/1990 | Welker | 73/863.83 |
| 4,934,201 | 6/1990 | Grimminger et al. | 73/863.11 |
| 4,942,772 | 7/1990 | Welker | 73/863.83 |
| 5,003,830 | 4/1991 | Spencer | 73/863.83 |

FOREIGN PATENT DOCUMENTS

| | | | |
|---|---|---|---|
| 2143045 | 8/1971 | Fed. Rep. of Germany | 73/863.84 |
| 2441844 | 11/1976 | Fed. Rep. of Germany | 73/863.83 |
| 0135692 | 11/1978 | Japan | 73/864.34 |

Primary Examiner—Robert Raevis
Attorney, Agent, or Firm—Bachman & LaPointe

[57] ABSTRACT

A recirculation device permits a relatively inaccessible fluid housed in a vessel having an access port to be evaluated externally of the vessel; the device provides a recirculating flow path extending from inside the vessel passing through the access opening to an external fluid loop, and back to the vessel via the same access opening; the flow path comprises an upstream path and a downstream path, which paths are discrete separate paths throughout their length; flow in the recirculating flow path is induced in the external fluid loop; the fluid can be sensed directly in the fluid loop or a sample can be removed from the loop for evaluation.

16 Claims, 3 Drawing Sheets

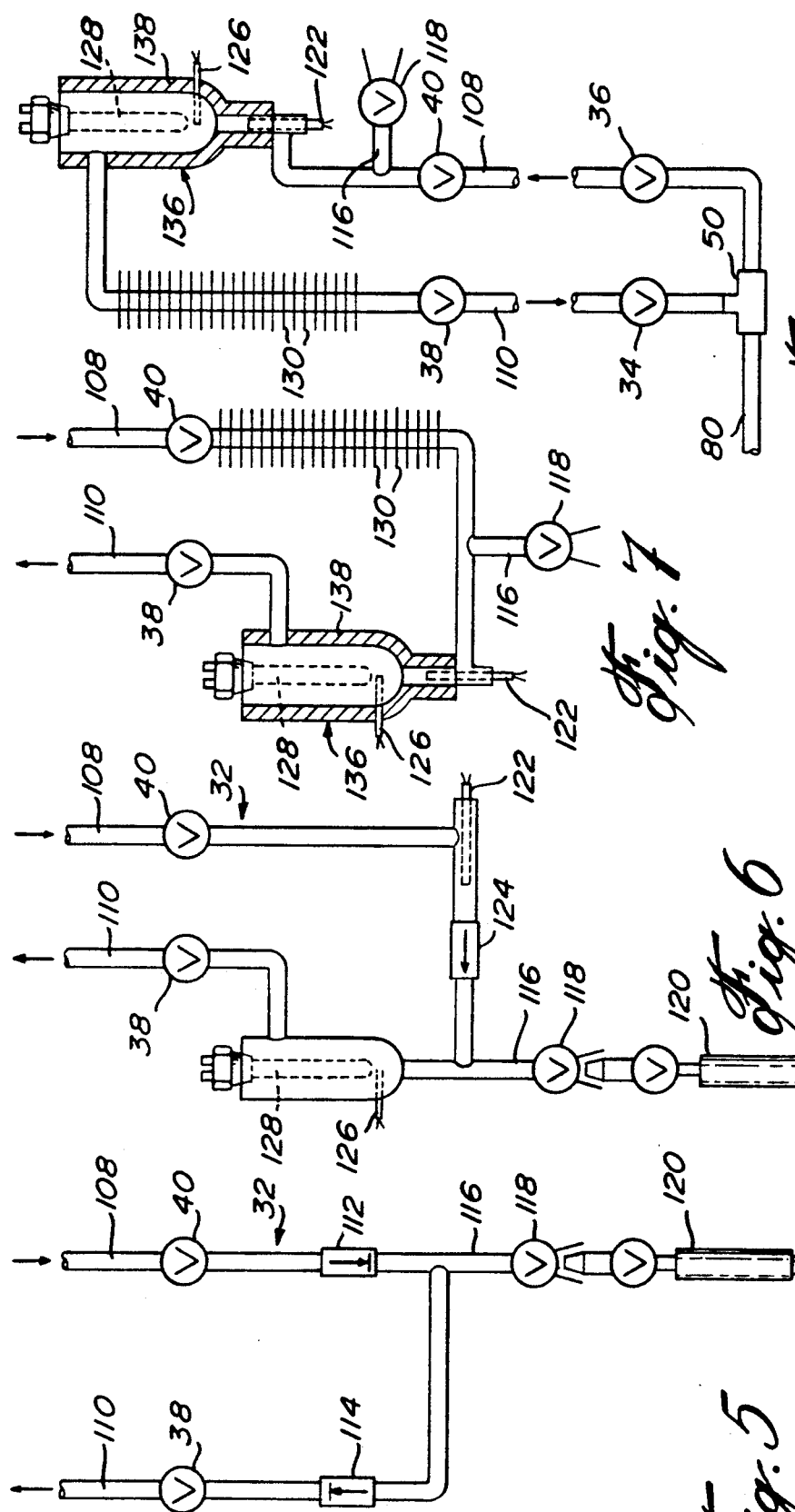

DEVICE AND METHOD FOR RECIRCULATING A STREAM OF FLUID FROM A VESSEL

BACKGROUND OF THE INVENTION i) Field of the Invention

This invention relates to a recirculating device and method for recirculating a stream of fluid from a vessel; the invention also relates to a recirculation conduit assembly which forms a subassembly of a recirculating device of the invention and to a combination of a vessel housing a fluid and a recirculating device of the invention.

ii) Description of Prior Art

One is frequently faced with the situation where it is desirable either to insert a sensor into a closed fluid filled tank to monitor some characteristic of the fluid or to be able to withdraw a representative sample of the fluid from the tank for subsequent analysis. If the tank cannot be emptied, fabrication of a suitable entry port for the sensor, is, in most cases, impossible. Even if such a port does exist, installation of a sensor without significant fluid loss is also difficult or impossible if the fluid level cannot be lowered.

Obtaining a representative fluid sample for independent analysis from a tank fitted only with a drain valve also presents problems since considerable fluid must be discarded to eliminate the stagnant fluid in the region of the valve. Even after such flushing, the final sample will still be taken from near the tank wall which may not be representative of the bulk fluid.

A representative example of this problem is the electrical transformer which comprises a closed tank housing an insulating oil. Such transformers have a long life, typically 20 years or more and most existing transformers are not equipped with an entry port permitting access to the oil for sensing parameters of the oil. Such sensing is now routinely employed as a means of detecting faults in the transformer, see, for example, Canadian Patent 1,082,774, issued July 29, 1980, James E. Morgan. Existing tanks do have a drainage port but removal of a fluid sample through such port results in the disadvantages indicated above.

SUMMARY OF THE INVENTION

It is an object of this invention to provide a recirculation device which permits withdrawal of a fluid stream from a tank having an access opening, such as a drainage port or filling port, and return of the stream to the tank through the same access opening.

It is a particular object of this invention to provide such a device in a closed tank having a single access opening such as a drainage port.

It is still a further object of the invention to provide such a recirculation device whereby fluid in a vessel, especially a closed vessel, can be sampled or sensed externally of the vessel, even though the fluid is relatively inaccessible, without waste or loss of fluid.

It is a further object of this invention to provide such a device having a sensor or sense a parameter of the fluid in the stream.

It is yet another object of this invention to provide such a device having means for sampling the fluid in the stream.

It is still a further object of this invention to provide a recirculation conduit assembly for use in a device of the invention.

It is yet still another object of this invention to provide a method of determining a property value of a fluid housed in a vessel.

It is still another object of this invention to provide in combination a recirculating device of the invention and a vessel housing a fluid.

In accordance with one aspect of the invention a device for recirculating a stream of fluid from a vessel has means defining an upstream fluid flow path and means defining a downstream fluid flow path; the flow paths being in communication to form a recirculating fluid flow path. The upstream path communicates with an interior of a vessel housing a fluid through an access opening of the vessel and the downstream path communicates with such an interior through the same access opening. The upstream and downstream flow paths are discrete separate paths throughout their length. Means is included in the recirculating flow path to induce flow of fluid from the vessel into the upstream path and back to the vessel via the downstream path.

In accordance with another aspect of the invention a method of determining a property of a fluid housed in a vessel having an access opening comprises inducing flow of a stream of fluid into a flow path extending from within the vessel remote from the access opening, through the access opening to a fluid loop located externally of the vessel and from the loop to the access opening, and back into the vessel, and detecting a property of the fluid in the flow loop.

DESCRIPTION OF PREFERRED EMBODIMENTS

The device of the invention has a number of advantages in preferred embodiments.

First the device may be installed in a fluid filled tank through any suitable ball or gate valve without any significant loss of fluid from the tank. Secondly fluid may be withdrawn from a sampling point situated well inside the tank. Thirdly tank fluid may be circulated through an external loop where it may be sampled or caused to flow past a sensor. Circulation may be effected by any convenient means, for example manual means, a mechanical circulating pump or a thermal gradient.

The fluid may be returned to the tank through the same access opening or valve but is discharged at a point physically separated from the sampling point thus eliminating or minimizing recirculation of the same portion of the fluid.

In a preferred embodiment a portion of the upstream flow path extending out of the vessel is disposed axially within, more especially concentrically within, the fluid exit end of the downstream flow path. Furthermore, this portion of the upstream flow path is axially movable or reciprocatible relative to the fluid exit end of the downstream flow path so as to provide a selected, desired spaced relationship between the entrance to the upstream flow path and the exit from the downstream flow path.

BRIEF DESCRIPTION OF DRAWINGS

The invention is illustrated in particular and preferred embodiments by reference to the accompanying drawings in which:

FIG. 5 illustrates schematically a portion of a recirculating device of the invention with a manual inducer of circulation.

FIG. 6 illustrates schematically a portion of a recirculating device of the invention in another embodiment incorporating a mechanical pump, a sensor and a sampler;

FIG. 7 illustrates schematically a portion of a recirculating device of the invention in yet another embodiment employing thermally induced circulation and incorporating a sensor; and FIG. 8 illustrates schematically a portion of a recirculating device of the invention in still another embodiment employing thermally induced circulation and incorporating a sensor.

DESCRIPTION OF PREFERRED EMBODIMENTS WITH REFERENCE TO THE DRAWINGS

Figure 1:
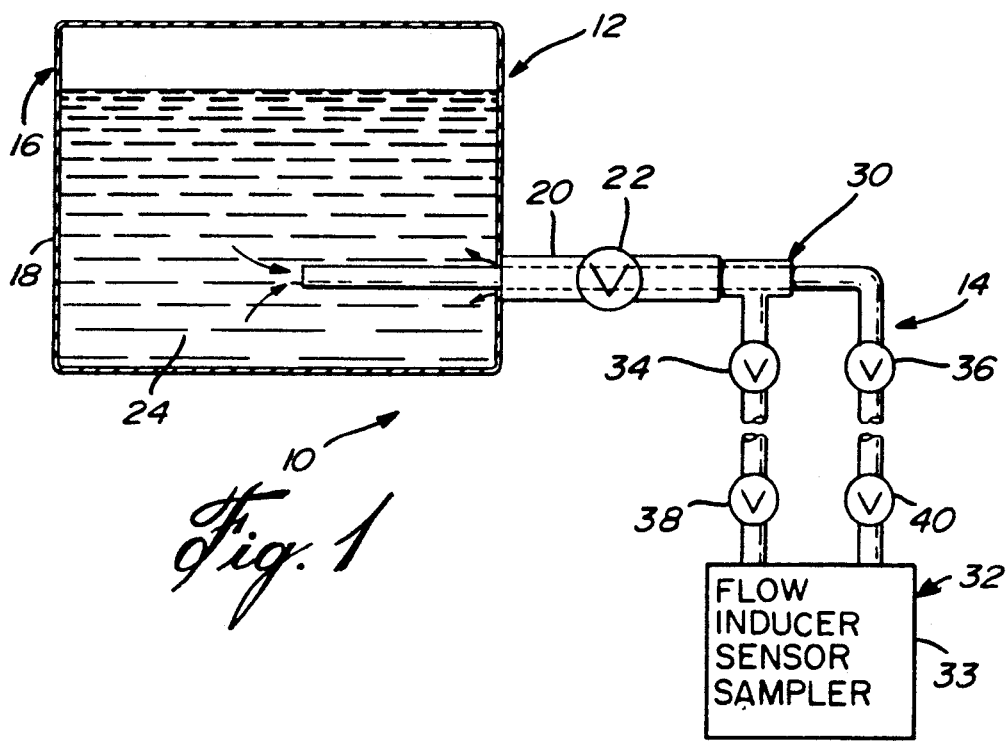
FIG. 1 illustrates schematically an assembly of a recirculating and sampling or sensing device, in accordance with the invention, connected to a vessel containing a fluid which is to be sampled or sensed.

With further reference to FIG. 1 a vessel installation 10 includes a closed vessel 12 and a recirculating device 14.

Closed vessel 12 comprises a tank 16 having a tank wall 18 with an access port 20 therein having a valve 22. A fluid 24 is housed in closed vessel 12.

Recirculating device 14 includes a recirculation conduit assembly 30 and a return loop 32. Conduit assembly 30 includes valves 34 and 36; and return loop 32 includes valves 38 and 40.

The return loop 32 includes a flow inducer and a sensor and/or sampler identified by block 33.

Figure 2:
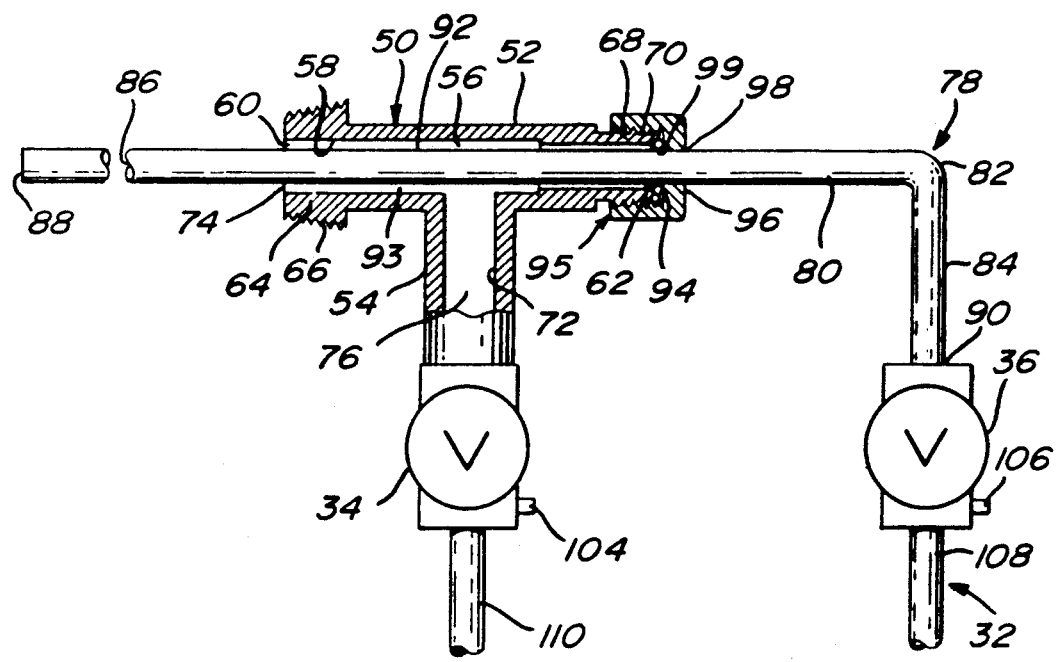
FIG. 2 illustrates schematically a conduit assembly of the invention for use in the device of FIG. 1.
Figure 3:
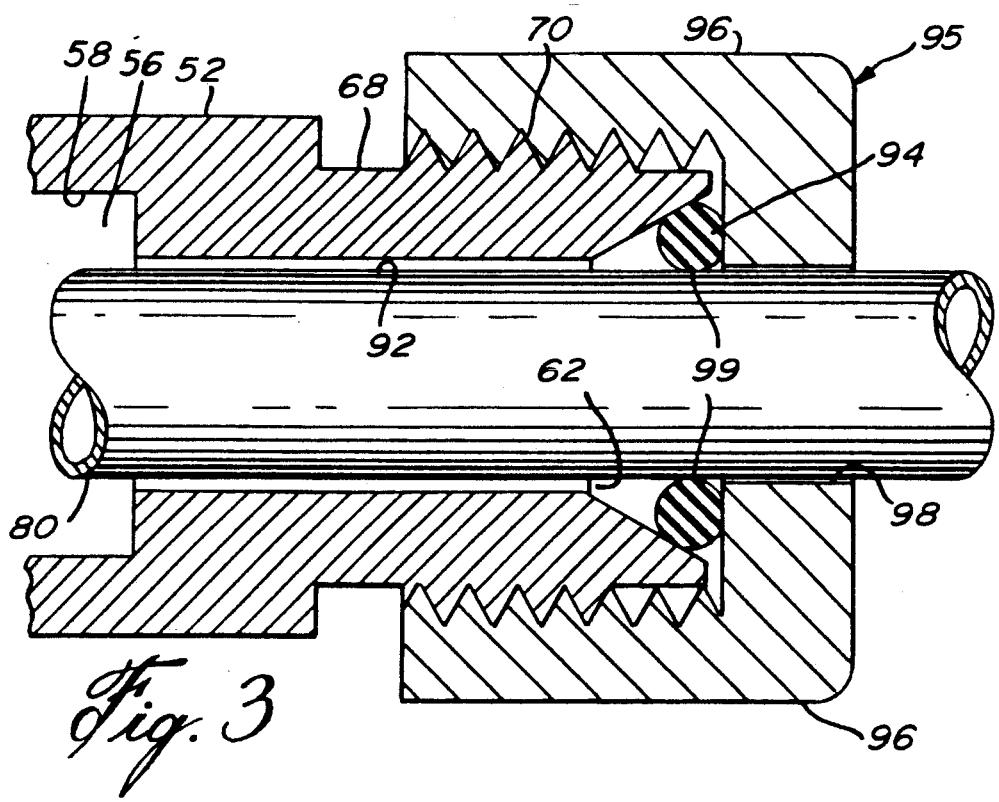
FIG. 3 shows a detail of the seal in the assembly of FIG. 2.

With further reference to FIGS. 2 and 3 details of recirculation conduit assembly 30 are illustrated.

Recirculation conduit assembly 30 includes a T-conduit 50 and a dip leg 78.

T-conduit 50 includes a head conduit 52 and a leg conduit 54 generally perpendicular to head conduit 52.

A bore 56 in head conduit 52 has a generally cylindrical bore wall 58 and terminates at opposed ends of head conduit 52 in opposed bore orifices 60 and 62, respectively.

Head conduit 52 has a tapered nose 64 with a thread 66 adjacent bore orifice 60. Head conduit 52 has a nose 68 with a thread 70 adjacent bore orifice 62.

Leg conduit 54 includes a bore 72 in flow communication with bore 56 intermediate bore orifices 60 and 62.

Bore orifice 60 defines a fluid outlet 74 in bore 56, and bore 72 defines a fluid inlet 76.

Dip leg 78 includes an elongate conduit 80, a conduit bend 82 and a conduit leg 84.

Flow passage 86 extends the length of dip leg 78 from an in-flow port 88 in conduit 80 to an out-flow port 90 in leg 84.

Elongate conduit 80 has a generally cylindrical conduit wall 92, and elongate conduit 80 extends axially of bore 56 such that an annular flow passage 93 is defined between conduit wall 92 and bore wall 58.

A seal 95 comprises an annular sealing ring 94, typically an O-ring, and a nut 96.

Nut 96 has a bore or orifice 98 and sealing ring 94 has a bore or orifice 99 by means of which nut 96 and annular sealing ring 94 are slidingly mounted on elongate conduit 80.

Valve 34 is mounted in fluid inlet 76 of leg conduit 54 and valve 36 is mounted in out-flow port 90 of dip leg 78. Valves 34 and 36 have bleed nipples 104 and 106 respectively.

An upstream flow line 108 of return loop 32 (see FIG. 1) is in flow communication with dip leg 78 through valve 36 and a downstream flow line 110 is in flow communication with bore 72 of leg conduit 54 via valve 34.

Figure 4A:
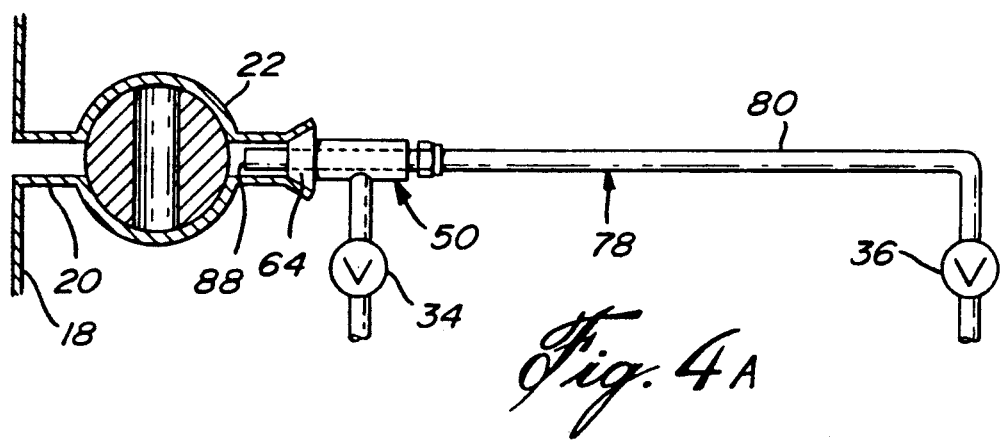
FIGS. 4A and 4B illustrate schematically the installation of the conduit assembly of FIG. 2 on a vessel as in FIG. 1.
Figure 4B:
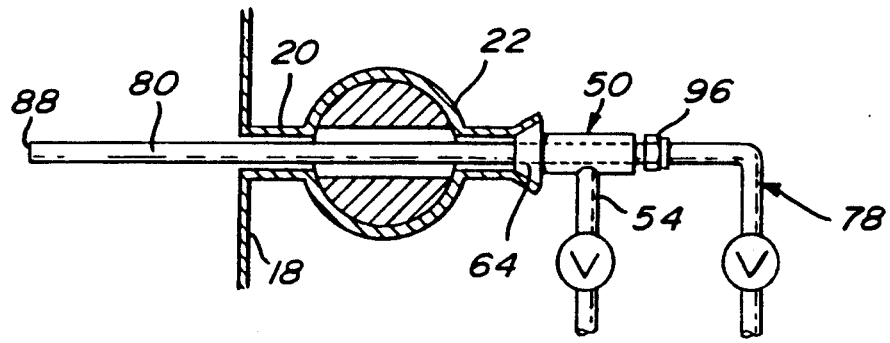

With further reference to FIGS. 4A and 4B there is illustrated schematically the mounting of recirculation conduit assembly 30 in the access port 20 of a tank 16, and the general operation is described further with reference to FIGS. 1, 2, 3, 4A and 4B.

In general it will be observed that the recirculating device 14 can conveniently be employed in any tank 16 which has an existing access port 20 and valve 22 with a straight through flow path.

In assembling the recirculation device 14, the T-conduit 50 is first connected to valve 22 by means of threaded nose 64. Elongate conduit 80 is then inserted through the sliding seal 95 and nut 96 tightened sufficiently to make a leak-tight seal but to still allow a sliding motion of elongate conduit 80. At this point valve 22 is still closed. After ensuring that valves 34 and 36 are closed, valve 22 is opened and elongate conduit 80 is slid forward along bore 56 until it passes completely through the valve 22 into the fluid 24. If desired, air trapped in recirculation conduit assembly 30 can be flushed out by first rotating the recirculation conduit assembly 30 so that the valves 34 and 36 are directed upwardly, and then partially opening these valves so that the fluid in the tank 16 can displace the trapped air.

The elongate conduit 80 slides along bore 56 relative to the seal 95 until a desired penetration of elongate conduit 80 and its inflow port 88 into the fluid 24 housed in tank 16 is achieved. The sliding movement is illustrated schematically in FIGS. 4A and 4B. Elongate conduit 80 slides relative to annular sealing ring 94 which is in sealing engagement with elongate conduit 80 and nose 68 as illustrated in FIG. 3.

Valves 34 and 36 are maintained closed during connection of the return loop 32.

Upstream flow line 108 is connected by any suitable means to valve 36 of recirculation conduit assembly 30 and downstream flow line 110 is similarly connected by any suitable means to valve 34 of leg conduit 54.

By suitable manipulation of valves 34, 36, 38 and 40, in conjunction with their associated bleed nipples, it is possible to flush all the air from lines 108 and 110 and from the recirculation loop 32 without allowing any air to enter the tank 16.

Once the entire external assembly is full of fluid and free from air, valves 34, 36, 38 and 40 are opened fully and then left open permanently to allow fluid circulation.

As particularly illustrated in FIG. 1, in-flow port 88 of elongate conduit 80 is remote from access port 20 of tank 16.

Flow of fluid 24 in tank 16 into in-flow port 88 is induced by a flow inducer in the return loop 32. Flow inducers of different types may be employed as will be discussed in more detail hereinafter.

Thus a fluid stream is developed from the interior of the bulk of fluid 24 in tank 16, and such fluid stream flows along elongate conduit 80 then to bend 82 and leg 84 into return loop 32. The fluid stream flows along return loop 32 and through fluid inlet 76 into bore 72 and from bore 72 into the annular flow passage 93 about elongate conduit 80. The fluid stream flows along annular flow passage 93, exits head conduit 52 at fluid outlet 74 and then flows through valve 22 and access port 20 back into tank 16.

As indicated by the flow arrows in FIG. 1, the fluid is returned to the tank 16 at a point remote from the point at which fluid is withdrawn into elongate conduit 80. If the in-flow port 88 were located in the region of access port 20, there would be a tendency for the same portion of fluid to be continuously recirculated and such fluid would not necessarily be representative of the fluid 24 in the interior of vessel 12.

During passage of the fluid stream along return loop 32 appropriate sensing of a parameter of the fluid may be carried out as desired, or a sample of the fluid may be withdrawn from return loop 32. It will be evident, however, that such sensing or withdrawal of a sample can be carried out during continuous recirculation of fluid so that a representative quantity of the fluid 24 can be sensed or a representative sample can be taken. It will also be evident that employing the recirculating device 14 in the vessel installation 10 permits sensing of a fluid without loss of fluid 24 from the closed vessel 12, and that likewise a sample of the fluid can be taken without loss of fluid 24 from the vessel 12, other than the quantity removed as a sample.

Thus a recirculating flow path is established commencing at in-flow port 88 and terminating at access port 20, the recirculating flow path comprises an upstream flow path commencing at port 88, the upstream flow path ending and the downstream flow path beginning at the flow inducer within schematic block 33 of FIG. 1 and terminating at port 20. The upstream and downstream flow paths are discrete and continuous through their length.

The fluid flow in annular flow passage 93 towards access opening 20 is essentially countercurrent to the flow in elongate conduit 80.

With further reference to FIG. 5 there is shown schematically a return loop 32 for use in the device 14 in which one-way check valves 112 and 114 are located in upstream flow line 108 and downstream flow line 110 respectively.

Leg 116 having a valve 118 is located downstream of one-way check valve 112.

Manual circulation of a fluid stream in the recirculating device 14 may be achieved by means of a piston syringe 120 introduced at leg 116. Valve 118 is opened and syringe 120 is in essence employed as a hand operated pump. Drawing out the syringe handle draws fluid into leg 116 and the barrel of syringe 120 through one-way check valve 112, thereafter pressing the handle of syringe 120 to expel the fluid, forces the fluid to flow from the upstream flow line 108 to the downstream flow line 110 in the direction of one-way check valve 114. The action of the one-way check valve 112 and 114 ensures that fluid is pulled into syringe 120 from the upstream flow line 108 and discharged into the downstream flow line 110. A sufficient number of strokes of syringe 120 is made to purge the upstream flow line 108 and so as to provide the syringe 120 filled with fluid 24 representative of the fluid 24 at the sampling point in the interior of tank 16. After closure of valve 118, the syringe 120 may be detached to expel the sample of fluid from the syringe 120 at a desired site of analysis.

It will be evident that obtaining a representative sample by this technique does not result in loss or waste of fluid.

With further reference to FIG. 6, there is shown a portion of return loop 32 having a heater 122, a mechanical circulating pump 124, a temperature control sensor 126 and a fluid monitoring sensor 128. The return loop 32 of FIG. 5 additionally employs a sampling region comparable to that of FIG. 4 and identified by means of the same integers.

The circulating pump 124 achieves the desired recirculation of fluid 24 from tank 16. Fluid flows along upstream flow line 108 past heater 122. Heater 122 may not be essential for all embodiments but may be necessary if the fluid monitoring sensor 128 requires a temperature controlled environment, and also if the circulating pump 124 requires that the fluid 24 be maintained within a certain viscosity range. Thus in an environment of lower ambient temperature the heater 122 may be required to ensure a sufficiently low viscosity for efficient pumping by circulating pump 124.

Thus in the embodiment of FIG. 6, fluid 24 heated to a desired temperature range by heater 122 flows past temperature control sensor 126 and fluid monitoring sensor 128 and back to the tank 16 via downstream flow line 110. The fluid monitoring sensor 128 may be any device capable of measuring or detecting a characteristic of the fluid 24. Heater 122 may be controlled, for example, switched on and off, responsive to temperature control sensor 126 to ensure that the fluid is maintained in a desired temperature range.

With further reference to FIG. 7 there is illustrated schematically a return loop 32 in which fluid flow is induced by a thermal gradient circulation.

Cooling fins 130 are mounted on upstream flow line 108. Downstream flow line 110 includes a heater 122, a temperature control sensor 126 and a sensing zone 136. Sensing zone 136 includes thermal insulation 138 and a fluid monitoring sensor 128.

In the embodiment of FIG. 7 there is shown a sampling section comparable to that of FIG. 4 identified by use of the same integers.

In the embodiment of FIG. 7 fluid in upstream flow line 108, if it is above ambient temperature, is cooled by means of the cooling fins 130, and fluid 24 in downstream flow line 110 is heated by means of heater 122, with insulation 138 preventing loss of heat from the fluid 24. In this way the fluid 24 in downstream flow line 110 is maintained at a higher average temperature than the fluid 24 in upstream flow line 108, with the result that a density differential is maintained between the fluid 24 in the upstream flow line 108 and the fluid 24 in the downstream flow line 110. By providing that the flow lines 108 and 110 extend for a sufficient vertical distance, a pressure differential is established which produces circulation in the desired direction.

With further reference to FIG. 8 there is shown a variant of the embodiment of FIG. 7 which may be employed if the return loop 32 is disposed at a position elevated with respect to the valve 22, so that in essence the recirculating device 14 is inverted relative to the configuration illustrated in FIG. 7. Thus in the embodiment of FIG. 8 in which like parts are identified with the same integers as in FIG. 7, the upstream flow line 108 contains the sensing zone 136, heater 122 and temperature control sensor 126 and the downstream flow line 110 contains the cooling fins 130. In this embodiment, efficient cooling of the descending fluid by the cooling fins 130 is essential for maintaining the desired flow. As discussed above the embodiments of both FIGS. 7 and 8 employing a thermal gradient to drive the fluid 24 in the recirculating device 14 require a sufficient vertical height of the upstream flow line 108 and the downstream flow line 110.

While reference has been made to a nut 96 as part of seal 95 in FIGS. 2 and 3, it will be understood that any convenient means of mounting or disposing the annular sealing ring 94 in the required sealing arrangement while permitting dip leg 78 to slide relative to ring 94 may be employed. The sliding arrangement has particular importance in the assembly and disassembly of the device 14 in vessel 12 because it permits such assembly and disassembly without loss of fluid from vessel 12. After assembly the rigidity of the return loop 32 is sufficient to prevent or minimize undesired sliding movement of dip leg 78 relative to ring 94.

Thus the present invention provides a relatively simple means whereby a fluid in a closed vessel can be sampled or sensed externally of the vessel, even though the fluid is relatively inaccessible, without waste or loss of fluid.

The invention has been described with reference to particular and preferred embodiments. It will be understood that modifications and alterations will occur to others upon a reading and understanding of this specification. The invention includes all such modifications and alterations in so far as they come within the scope of the claims or the equivalents thereof.

I claim:

1. A device which is removably mountable in an access opening in a wall of a vessel housing a fluid in an interior of the vessel, said access opening being in fluid flow communication with the interior of the vessel, and below the fluid level of the vessel, said device serving to recirculate a stream of fluid from the vessel through the access opening, without waste or inadvertent loss of fluid during the recirculation of the stream, or during mounting of the device in the access opening, or removal therefrom comprising:

an upstream conduit defining an upstream fluid flow path adapted to communicate with the interior of a body of fluid in an interior of a vessel housing the fluid, through said access opening of the vessel, a downstream conduit defining a downstream fluid flow path communicating with the interior of the vessel through said access opening, said downstream fluid flow path having an outlet end, said upstream and downstream flow paths being in fluid flow communication to define a recirculating fluid flow path, said upstream conduit having a fluid in-flow port and downstream conduit having a fluid outlet at said outlet end of said downstream flow path, means in said recirculating fluid flow path to induce flow of fluid from the vessel into said upstream path and back to the vessel via said downstream path, said upstream and downstream paths being discrete separate paths throughout their length, said outlet end of said downstream fluid flow path comprising an annular flow path surrounding a portion of said upstream flow path, and an annular seal member sealingly disposed between said upstream conduit and said downstream conduit, said upstream conduit being slidable relative to said annular seal member to adjustably space said in-flow port of said upstream conduit from said fluid outlet of said downstream conduit such that recirculating fluid is returned to the vessel interior at said fluid outlet remote from said in-flow port, thereby eliminating or minimizing recirculation of the same portion of fluid, said annular seal member permitting said mounting of said device in said access opening and said removal therefrom without waste or loss of fluid.

2. A device according to claim 1, wherein said means to induce flow comprises a mechanical circulating pump.

3. A device according to claim 1, wherein said recirculating fluid path has first and second spaced apart one-way check valves therein which permit fluid flow in the recirculating fluid path solely in the flow direction towards said outlet end, and said means to induce flow comprises a manually operated pumping means communicating with said recirculating fluid path intermediate said first and second one-way check valves.

4. A device according to claim 3, wherein said pumping means comprises a piston syringe.

5. A device according to claim 1, wherein said means to induce flow comprises means to establish a thermal gradient effecting a density differential in fluid in upstream and downstream zones of said recirculating fluid path.

6. A device according to claim 1, further including sensing means in said recirculating fluid path, said sensing means being adapted to sense a characteristic of a fluid in said recirculating fluid path.

7. A device according to claim 6, further including heating means adapted to heat a fluid in said recirculating fluid path to maintain fluid arriving at said sensing means at a desired temperature.

8. A device according to claim 1, further including means in said recirculating fluid path for removing a sample of a fluid in said recirculating path.

9. In combination a vessel housing a body of fluid in an interior of the vessel and a device removably mounted in an access opening of said vessel, said vessel having a vertical vessel wall with said access opening therein, below the fluid level of the vessel, and a flow valve in said access opening, said device comprising an upstream conduit defining an upstream fluid flow path adapted to communicate with the interior of said body of fluid in said vessel housing the fluid, through said access opening of the vessel, a downstream conduit defining a downstream fluid flow path communicating with the interior of the vessel through said access opening, said downstream fluid flow path having an outlet end, said upstream and downstream flow paths being in fluid flow communication to define a recirculating fluid flow path, said upstream conduit having a fluid in-flow port and said downstream conduit having a fluid outlet at said outlet end of said downstream flow path, means in said recirculating fluid flow path to induce flow of fluid from the vessel into said upstream path and back to the vessel via said downstream path, said upstream and downstream paths being discrete separate paths throughout their length, said outlet end of said downstream fluid flow path comprising an annular flow path surrounding a portion of said upstream flow path, and an annular seal member sealingly disposed between said upstream conduit and said downstream conduit, said upstream conduit being slidable relative to said annular-seal member to adjustably space said in-flow port of said upstream conduit from said fluid outlet of said downstream conduit, said annular seal member permitting said device to be removably mounted in said access opening without waste or accidental loss of fluid in said vessel and with said upstream and downstream flow paths communicating with said body of fluid in said vessel through said access opening, such that recirculating fluid is returned to the vessel at said fluid outlet remote from said in-flow port, thereby eliminating or minimizing recirculation of the same portion of fluid.

10. A combination according to claim 9, wherein said vessel is a closed vessel and said access opening is the sole access opening.

11. In combination a vessel housing a body of fluid in an interior of the vessel and a device removably mounted in an access opening of said vessel, said vessel having a vertical vessel wall and an access opening in said wall, below the fluid level of the vessel, and a flow valve in said access opening, said device comprising:

an outlet conduit member for return of fluid to said vessel and an inlet conduit member for removal of fluid from said vessel, said outlet conduit member having first and second opposed ends and a bore having a bore wall extending from said first end to said second end, said bore having a fluid inlet intermediate said first and second ends and a fluid outlet at said first end, said inlet conduit member having an in-flow passage therein extending from an in-flow port to an out-flow port, said inlet conduit member extending axially along said bore in spaced apart relationship with said bore wall, said in-flow port and said out-flow port being remote from said bore, and said spaced apart relationship defining an annular out-flow passage between said bore wall and said inlet conduit member, said inlet conduit being substantially concentrically within said outlet conduit member, a fluid return conduit means connecting said out-flow port of said inlet conduit member and said fluid inlet of said outlet conduit member, means in said fluid return conduit means to induce flow of fluid from the vessel into said in-flow port and along a flow path back to the vessel sequentially via said in-flow passage, fluid return conduit means, annular out-flow passage and fluid outlet, and sealing means providing a seal between said second end of said bore, and said inlet conduit member, said sealing means comprising an annular seal member disposed in sealing engagement with said bore wall and said inlet conduit member at said second end of said bore, said inlet conduit member being slidable relative to said annular seal member to space said in-flow port from said fluid outlet such that recirculating fluid is returned to the vessel interior at said fluid outlet remote from said in-flow port, thereby eliminating or minimizing recirculation of the same portion of fluid, said device being removably mounted in said access opening without waste or accidental loss of fluid in said vessel and with said outlet conduit member being mounted in said access opening and said inlet conduit member extending through said outlet conduit member into said fluid in said vessel, said in-flow port of said inlet conduit member being remote from said fluid outlet of said outlet conduit member, such that recirculating fluid is returned to the vessel at said fluid outlet remote from said in-flow port, thereby eliminating or minimizing recirculation of the same portion of fluid.

12. A combination according to claim 11, wherein said device further includes a sensor in said flow path, external of said vessel, effective to sense a characteristic of the fluid.

13. A combination according to claim 12, wherein said vessel is an electrical transformer tank, said fluid is an insulating fluid and said access opening is a drainage port or filling port of said tank.

14. A method of determining a property or characteristic of a fluid housed in a vessel having a vertical wall and an access opening in said vertical wall below the fluid level of said vessel, said access opening having a valve in a valve housing and being in fluid flow communication with the fluid in the vessel comprising:

removably mounting a fluid recirculation device in said access opening without waste or accidental loss of fluid in said vessel, while maintaining said valve in said valve housing closed, said device having an upstream conduit defining an upstream fluid flow path for communicating with fluid int he interior of the vessel, and a downstream conduit defining a downstream fluid flow path communicating with the interior of the vessel, said upstream conduit extending concentrically within said downstream conduit, said upstream and downstream flow paths being in fluid flow communication to define a recirculating fluid flow path, said upstream conduit having a fluid in-flow port and said downstream conduit having a fluid outlet, an annular seal member sealingly disposed between said upstream conduit and said downstream conduit, opening said valve and slidably moving said upstream conduit relative to said annular seal member through said valve housing and access opening into said vessel, to space said in-flow port remotely from said fluid outlet in said fluid, inducing flow of a stream of the fluid into said in-flow port to said flow path from within the vessel remote from said fluid outlet along said fluid flow path to said fluid outlet and into said vessel, and detecting a property or characteristic of the fluid in said recirculating fluid flow path, the spacing of said in-flow port from said fluid outlet being such that recirculation of the same portion of fluid is eliminated or minimized.

15. A method according to claim 14, which comprises continuously flowing fluid from said vessel along said recirculating fluid flow path and sensing a property of the fluid flowing in said recirculating fluid flow path.

16. A method according to claim 14, in which said detecting comprises withdrawing a sample of fluid from said recirculating fluid flow path and evaluating a property of the fluid sample.

* * * * *